United States Patent
Norris et al.

(10) Patent No.: US 6,669,631 B2
(45) Date of Patent: Dec. 30, 2003

(54) DEEP COMPUTING APPLICATIONS IN MEDICAL DEVICE SYSTEMS

(75) Inventors: Harry Eldrige Norris, Shorewood, MN (US); Chester G. Nelson, Plymouth, MN (US)

(73) Assignee: Medtronic, Inc., Minneapolis, MN (US)

(*) Notice: Subject to any disclaimer, the term of this patent is extended or adjusted under 35 U.S.C. 154(b) by 297 days.

(21) Appl. No.: 09/881,268

(22) Filed: Jun. 14, 2001

(65) Prior Publication Data

US 2002/0026103 A1 Feb. 28, 2002

Related U.S. Application Data

(60) Provisional application No. 60/211,410, filed on Jun. 14, 2000.

(51) Int. Cl.[7] .................................................. A61B 5/00
(52) U.S. Cl. ............................ 600/300; 705/3; 128/923
(58) Field of Search ............................. 600/300; 705/3; 607/27, 30, 60; 604/891.1; 128/903, 923, 924

(56) References Cited

U.S. PATENT DOCUMENTS

| | | | |
|---|---|---|---|
| 4,494,950 A | 1/1985 | Fischell | 604/66 |
| 4,886,064 A | 12/1989 | Strandberg | 128/419 PG |
| 4,987,897 A | 1/1991 | Funke | 128/419 PG |
| 5,331,966 A | 7/1994 | Bennett et al. | 128/696 |
| 5,345,362 A | 9/1994 | Winkler | 361/681 |
| 5,390,238 A | 2/1995 | Kirk et al. | 379/93 |
| 5,544,661 A | 8/1996 | Davis et al. | 128/700 |
| 5,564,434 A | 10/1996 | Halperin et al. | 128/748 |

(List continued on next page.)

FOREIGN PATENT DOCUMENTS

| | | | | |
|---|---|---|---|---|
| EP | 0 761 255 A1 | 3/1997 | .......... | A61N/1/372 |
| WO | 9802209 | 1/1998 | .......... | A61N/1/375 |
| WO | WO 98/15910 | 4/1998 | .......... | G06F/19/00 |
| WO | WO 98/39061 | 9/1998 | .......... | A61N/1/39 |
| WO | 9914882 | 3/1999 | | |
| WO | 9941682 | 8/1999 | .......... | G06F/17/30 |
| WO | 0070529 | 11/2000 | .......... | G06F/19/00 |

OTHER PUBLICATIONS

Dijk et al., "Central Pacemaker Patients Registration in the Netherlands A 10 Year Evaluation," *IEEE*, p. 293–296 (1990).

Porenta et al., "When Rats Meet Hearts: A Gopher Information Server for Cardiology," *IEEE*, p. 567–570 (1993).

*Primary Examiner*—Andrew M. Dolinar
(74) *Attorney, Agent, or Firm*—Girma Wolde-Michael; Michael G. Soldner

(57) ABSTRACT

Deep computing techniques are employed to mine statistical data bases and patient specific data files contributed from multiple sources, including implantable medical devices (IMDs) and external medical devices and other sources, to formulate patient-specific monitoring, diagnostic, therapeutic and educational information and to deliver the patient-specific diagnostic, therapeutic and educational information to the patient and/or patient health care provider. The present invention advantageously provides patient-specific information for IMD bearing patients that draws upon worldwide expertise and knowledge of IMDs of the type implanted, the patient's disease etiology, the drugs prescribed to the patient, the knowledge of experts in the field, and the optimal modes of operating the IMD to monitor physiologic conditions or apply therapies as reported by experts and medical device manufacturers. Patient data is supplied to a patient file at a centralized information database, the patient data including IMD developed patient data. Statistical data from public domain databases and governmental and international health agency databases is accessed. Deep computing techniques are applied to mine the accessed statistical data to associate pertinent statistical data with the patient data in the patient file to form a patient specific medical profile. Based upon the patient specific medical profile, patient specific information is formulated and delivered to one or more of the patient and the health care provider providing care to the patient.

38 Claims, 6 Drawing Sheets

U.S. PATENT DOCUMENTS

| | | | |
|---|---|---|---|
| 5,713,350 A | 2/1998 | Yokota et al. | 128/630 |
| 5,752,976 A | 5/1998 | Duffin et al. | 607/32 |
| 5,875,285 A | 2/1999 | Chang | 395/62 |
| 5,908,383 A | 6/1999 | Brynjestad | 600/300 |
| 5,997,476 A | 12/1999 | Brown | 600/300 |
| 6,067,542 A | 5/2000 | Carino, Jr. | 707/4 |
| 6,083,248 A | 7/2000 | Thompson | 607/30 |
| 6,221,011 B1 | 4/2001 | Bardy | 600/300 |
| 2002/0128866 A1 * | 9/2002 | Goetzke et al. | 705/2 |
| 2002/0165737 A1 * | 11/2002 | Mahran | 705/3 |

* cited by examiner

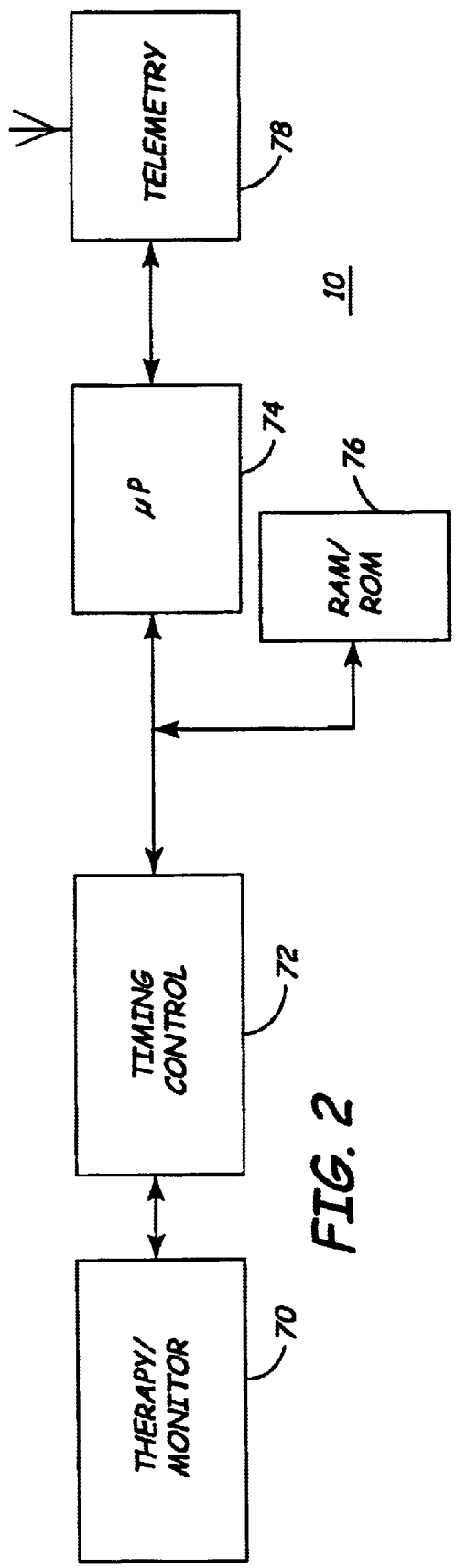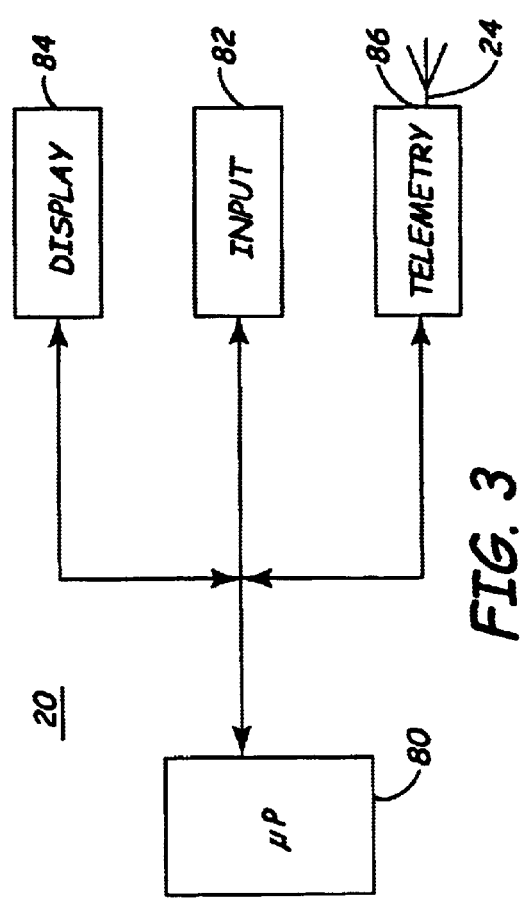

DEEP COMPUTING APPLICATIONS IN MEDICAL DEVICE SYSTEMS

This application claims priority from Provisional Application No. 60/211,410 filed Jun. 14, 2000.

FIELD OF THE INVENTION

The present invention pertains to deep computing applications in medical device systems, and particularly employing deep computing techniques to derive statistical data bases and patient specific data files contributed from multiple data repositories, including implantable medical devices (IMDs), external medical devices and other sources, to formulate patient specific medical history monitoring, diagnostic, therapeutic and educational information and to deliver the information to the patient and/or patient health care provider.

BACKGROUND OF THE INVENTION

A wide variety of IMDs have been developed for use in the human body to monitor a patient's condition and/or to treat a patient's underlying disease states. Such IMDs include implantable cardiac pacemakers, implantable cardioverter/defibrillators (ICDs), pacemaker/cardioverter/defibrillators, cardiomyostimulators, drug delivery systems, cardiac and other physiologic monitors, electrical stimulators including nerve, muscle, and deep brain stimulators, cochlear implants, and heart assist IMDs or pumps, etc.

At present, a wide variety of IMDs are commercially released or proposed for clinical implantation that are programmable in a variety of operating modes and are interrogatable using RF telemetry transmissions in telemetry sessions initiated between the IMD and an externally-located medical device (EMD). The terms "telemeter", "telemetry transmission" and the like are intended to embrace any action and manner of communicating and conveying patient or physiologic data and downlink telemetry data between the IMD and any type of EMD in the bi-directional uplink and downlink telemetry transmissions.

Typically, certain therapy delivery and monitoring operational modes and parameters of the IMD are altered temporarily or chronically in a non-invasive (i.e. non-surgical) manner using downlink telemetry transmission from an EMD of programming and interrogation commands or downlink messages herein also referred to as "downlink telemetry data". Moreover, a wide variety of real time and stored physiologic data as well as non-physiologic, IMD related, data or previously stored implant data (referred to collectively herein as "IMD developed patient data") composed into uplink messages and are uplink telemetered by the IMD to the EMD in response to a downlink telemetered interrogation command that is received by the IMD transceiver.

The EMD is typically characterized as a full function or limited function "programmer". The full function programmers are implemented with a full range of programming and interrogation capabilities and are intended for use by a physician or other health care provider to communicate with the IMD. In certain instances, patients are provided with limited function programmers (really wouldn't refer to a remote monitor/transponder as a "programmer") that typically have a limited range of programming functions (or no programming functions at all—like an RF head connected to a modem) and are intended for use by the patient to downlink telemeter a command to the IMD to deliver a therapy or change a therapy and/or to store physiologic data when the patient experiences particular symptoms or send a command instructing the IMD to "upload" stored data.

Such a two-way telemetry session is typically initiated in the presence of a health care provider that is a treating or implanting physician or a physician's assistant or the like, who is technically and medically trained sufficiently to operate the programmer, safely reprogram an operating mode or parameter of the IMD, and initiate uplink telemetry of patient data. Normally, this is done in a clinic, hospital room or physician's office at implant and periodically as deemed advisable during the time that the IMD remains implanted. The patient may have to travel a distance and take time away from employment to participate in the telemetry session. The patient would have to stay under medical care indefinitely if the medical conditions of the patient warrant continuous monitoring of the IMD.

Multiple generations of IMDs of each type may be implanted in the worldwide patient population at any given time because new IMD types and IMD generations are constantly being introduced while longevity of previously implanted IMDs continues to increase. Typically, each new generation of IMD offers more operating modes, parameters, and patient data storage capacity than its predecessor. Consequently, the types and volume of patient data that can be accumulated or sampled in use also increases, placing additional requirements on the telemetry and programming functions that are to be managed by health care providers using the supplied programmer. Thus, health care providers find it necessary to frequently upgrade their training in evaluating new patient candidates, diagnosing their medical condition, prescribing the proper IMD, and then in programming its operating modes and parameters and monitoring features in order to provide the optimum therapy and obtain useful patient data over time.

Moreover, the types of patient data that are developed by various sensors and operating systems of IMDs continue to expand. One such implantable EGM monitor for recording the cardiac electrogram from electrodes remote from the heart as disclosed in commonly assigned U.S. Pat. No. 5,331,966 and PCT publication WO 98/02209 is embodied in the Medtronic® REVEAL® Insertable Loop Recorder having spaced housing EGM electrodes. More elaborate implantable hemodynamic monitors (IHMs) for recording the EGM from electrodes placed in or about the heart and other physiologic sensor derived signals, e.g., one or more of blood pressure, blood gases, temperature, electrical impedance of the heart and/or chest, and patient activity have also been proposed. The Medtronic® CHRONICLE® IHM is an example of such a monitor that is coupled through a lead of the type described in commonly assigned U.S. Pat. No. 5,564,434 having capacitive blood pressure and temperature sensors as well as EGM sense electrodes. Such implantable monitors when implanted in patients suffering from cardiac arrhythmias or heart failure accumulate date and time stamped data that can be of use in determining the condition of the heart over an extended period of time and while the patient is engaged in daily activities. A wide variety of other IMDs have been proposed to monitor many other physiologic conditions as set forth in U.S. Pat. No. 6,221,011.

In addition, while the typical patient receives only one such IMD, there is growing realization that more than one such IMD may be implanted in a single patient as suggested in commonly assigned U.S. Pat. No. 4,987,897 and in U.S. Pat. Nos. 4,886,064 and 4,494,950, for example. For example, IMDs such as an ICD or a pacemaker, a neurological implant, a drug pump, a separate physiologic monitor and various other IMDs may be implanted into a single patient. As suggested in the '897 patent, it may be preferred to have an operable communication between the various IMDs to provide a coordinated clinical monitoring and therapy to the patient on a real-time basis.

In many cases drug regimens are also prescribed for patients having IMDs, and the health care provider must monitor and manage both the prescribed drug therapies and the IMD functions.

Continuous updating and monitoring of the IMDs is necessary to successfully manage the operations and assess the performance of each IMD in the patient receiving one IMD, much less multiple IMDs and interactions with drug therapies. There is a need to monitor the performance of the IMDs on a regular, if not a continuous, basis to ensure optimal patient care. In the absence of other alternatives, this imposes a great burden on the patient if a hospital or clinic is the only center where the necessary frequent follow up, evaluation and adjustment of the IMDs could be made. Moreover, even if feasible, an increasing number of health care providers and increased numbers of service areas or clinic centers would be required to provide adequate medical care to the burgeoning number of patients implanted with one or more IMD worldwide.

Medical care providers are also burdened by the need to continually remain abreast of the advancement of medical science, particularly medical advances or failures in diagnosis and treatment of the patient population under their care as well as disease trends. A wide variety of national and international professional, governmental, research and educational institutions and agencies exist to provide information and training to medical care providers. For example, the National Institutes of Health and the Centers for Disease Control conduct research and accumulate data into statistical databases that are employed by researchers to analyze disease trends and inform the medical community. This body of "medical knowledge" accumulates at a rapid pace and must be disseminated to the medical community in a timely and effective manner.

As patient population, medical knowledge, and IMD technology expand exponentially, costs also increase such that considerable efforts are brought to bear to make the provision of health care far more efficient and cost effective. A wide variety of initiatives have been undertaken to control costs. Substantial increases in productivity and quality have been associated with the computerization of the work place and the proliferation of information technologies that involve transmission of information between computers leading to a lowering of costs in many industries. Multiple types or combination of network architectures have been put into place, including community access television (CATV) networks, the public switched telephone network (PSTN), the integrated services digital network (ISDN), the Internet, local area networks (LAN), wide area networks (WAN), wireless communications networks, asynchronous transfer mode (ATM) networks, etc, to facilitate such data transmission. Software and hardware developments have also increased the computing and data transmission capabilities of servers, computer workstations, personal computers, and the ever-increasing variety of other peripheral devices capable of accessing a network leading to "pervasive computing".

These developments are being brought to bear in the effort to control the costs of medical and health care, particularly of patients who are not confined to a health care facility, in a wide variety of ways. Over the years, many systems have been advanced for remote monitoring of patients through radio or telephone communication or "telemedicine" links as disclosed, for example, in U.S. Pat. No. 5,544,661. More recently, systems for effecting interactive communication and remote monitoring of ambulatory patients have been proposed employing Internet based information technologies as disclosed in U.S. Pat. No. 5,997,476 and in PCT Publication Nos. WO 99/14882 and WO 99/41682, for example. Various systems have been proposed to provide medical information and assistance to patient subscribers to Internet based services as disclosed in PCT Publication No. WO 00/70529, for example.

Other systems have been proposed for assembling large scale integrated database management systems for patient data that can be accessed by subscribers in the health care field to obtain information pertinent to the treatment of a patient under their care as described in U.S. Pat. No. 6,067,542 and other articles and patents referenced therein. The '542 patent discloses data mining techniques for performing outcomes research against the consolidated patient records in the database to evaluate the critical pathways. Other data mining techniques applicable to medical research are disclosed in U.S. Pat. Nos. 5,875,285 and 5,908,383.

Advances in computing and information technologies have also been contributed to the design and manufacture of the above-described IMDs and programmers. Virtually all IMDs and external programmers providing the telemetry capability have a microcomputer-based architecture. These advances have enabled the above-described proliferation of types of IMDs and advancement in their capabilities while tending to not increase their costs.

It has been recognized that there is a need to reduce the cost of conducting telemetry sessions that are borne by the medical care provider and imposed on the patient in terms of lost work time. Moreover, it has been recognized that the information technologies and available networks introduce the possibility of chronic and continuous monitoring of IMDs wherever the IMD-bearing patient may happen to be at any given time as set forth, for example, in commonly assigned U.S. Pat. Nos. 5,752,976 and 6,083,248.

Thus, a number of proposals have been advanced to facilitate conducting telemetry sessions with IMDs virtually automatically employing information technologies and available networks of the types listed above. Typically, a central database and communications center is manned by a staff that initiates a remote telemetry session and oversees the collection of the data and analyzes it. For example, it has been proposed in the above-referenced '011 patent that a wide variety of patient data be automatically collected from an IMD in a patient, transmitted over an available network to a remote center, and maintained in a patient care record in a centralized database at the center. Baseline and updated patient data are maintained in the patient care record by a database server. The patient data is manipulated to make a determination of patient "wellness".

There remains a need to assist the medical care provider in managing such patients (and the associated data) having a variety of disease syndromes and implanted with one or more IMD of the types described having broad capabilities of providing an ever-increasing amount of IMD developed patient data in light of other patient data derived from other sources, IMD data available from manufacturer's and government sources, and the large body of general healthcare information. There remain unmet needs to provide for the integration, structuring, and analytical processing of the vast bodies of IMD data, patient data, and general healthcare information in order to develop and deliver new and unique clinical tools to help physicians better manage chronically ill patients, e.g., to improve diagnosis, monitoring, to assess therapy effectiveness and to optimize the monitoring and therapy deliveries by the IMDs.

SUMMARY OF THE INVENTION

In view of the above need, the present invention provides a system and method of managing the medical care of a patient having one or more IMD implanted in the patient's body to deliver a therapy and/or monitor a physiologic condition of the patient and capable of communicating patient data externally to a remote receiver. The receiver is in communication with a centralized medical information network that is capable of developing and delivering new and unique clinical tools to help physicians better manage chronically ill patients.

The centralized medical information network has a centralized database and accepts the IMD-developed patient data, and also receives, or has access to, other patient data derived from other sources. This may include IMD data available from manufacturers and government sources, and the large body of general healthcare information in established public domain databases, governmental repositories, and international health agency databases. Deep computing technologies are then applied to the assembled body of data to develop and provide patient-specific information to the health care provider, the patient, or the patient's family.

The present invention advantageously provides patient-specific information for IMD-bearing patients that draws upon worldwide expertise and knowledge of IMDs of the type implanted, the patient's disease etiology, the drugs prescribed to the patient, the knowledge of experts in the field, and the optimal modes of operating the IMD to monitor physiologic conditions or apply therapies as reported by experts and medical device manufacturers.

The present invention in one embodiment operates by providing patient data to a patient file at a centralized information database. The patient data includes IMD-developed patient data received from the IMD. Statistical data from public domain databases such as governmental and international health agency repositories is also obtained. Then deep computing techniques are applied to mine the accessed statistical data to associate pertinent statistical data with the patient data in the patient file to form a patient-specific medical profile. Further, based upon the patient-specific medical profile, the invention formulates patient-specific information, and delivers the formulated patient-specific information to one or more of the patient and the health care providers that is providing care to the patient.

The applying step further comprises applying one or more of algorithmic design and analysis, mathematical modeling and trend analysis, statistical estimation, and data/pattern recognition to the statistical data based upon the patient data to effect the association of relevant statistical data with the patient data to form the patient specific medical profile. This profile allows the most effective therapy regimen to be implemented. Further, predictive models are implemented using a derived patient profile to prospectively anticipate future health problems and recommend a proactive/pre-emptive course of action. Some of the deep computing analytical techniques that could be applied to the assembled database include data mining (extracting useful information from very large sets of data); interpolation and approximation (for estimating the trends of dynamic systems such as patient status improving or worsening); pattern discovery (finding recurring patterns in large, continuous streams of information, particularly continually developed patient data from the IMD (such as an EGM, or pressure waveforms); text mining (machine reading of textual information to discover insights e.g. from patient histories or subjective assessments); neural networks and fuzzy logic (expert systems and relational databases based on predictive algorithms); cluster analysis (determining the meaning of low frequency events that possess similarities); pattern discovery (understanding new meaning from analysis of patterns such as those inherent in EKG's, cardiac pressure waveforms, etc.); and other statistical methods and predictive algorithms related to low and high frequency data events.

The patient data provided to the patient file can include patient laboratory test data of laboratory tests of the patient, clinical test data of clinical tests of the patient, pharmaceutical prescription data of drugs prescribed for the patient, other care provider data accumulated by the care providers providing medical care to the patient, physical examination records and patient reported symptoms.

The patient data derived from sources other than the IMD developed patient data and provided to the patient file, can include the patient's genomic data (DNA) and other relevant clinical information developed about the patient, including all patient records, prescribed drug regimens and data derived from interviews with the patient and the patient's family, and other data collected in the home or elsewhere about the patient's status, e.g., family histories, weight, glucose results, etc., e.g., by telephone data entry. In the cardiac monitoring context, significant information about drug interaction and heart irregularities could be correlated with specific DNA signatures. Gene expression tools used to study drug-disease interactions can be extended to develop diagnostic algorithms, monitoring indicators and individual therapies based on deeper knowledge resulting from integrating and analyzing gene expression profiles with IMD developed patient data, drug regimens, and other relevant clinical/patient information. Gene expression tools may also be used to proactively design therapy regimens based on genetically-inherited latent health problems.

The formulating step further comprises formulating one or more of an individualized care plan, tailored action plans and reminders, progress reports, tailored rules by patients, physician and disease state, and automatically generated and communicated messages and alerts.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 2 is a block diagram representing the major components of an IMD of FIG. 1;

FIG. 3 is a block diagram presenting the major components of a programmer or webtop unit of FIG. 1;

DETAILED DESCRIPTION OF THE PREFERRED EMBODIMENTS

In the following detailed description of the preferred embodiments, reference is made to the accompanying drawings that form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
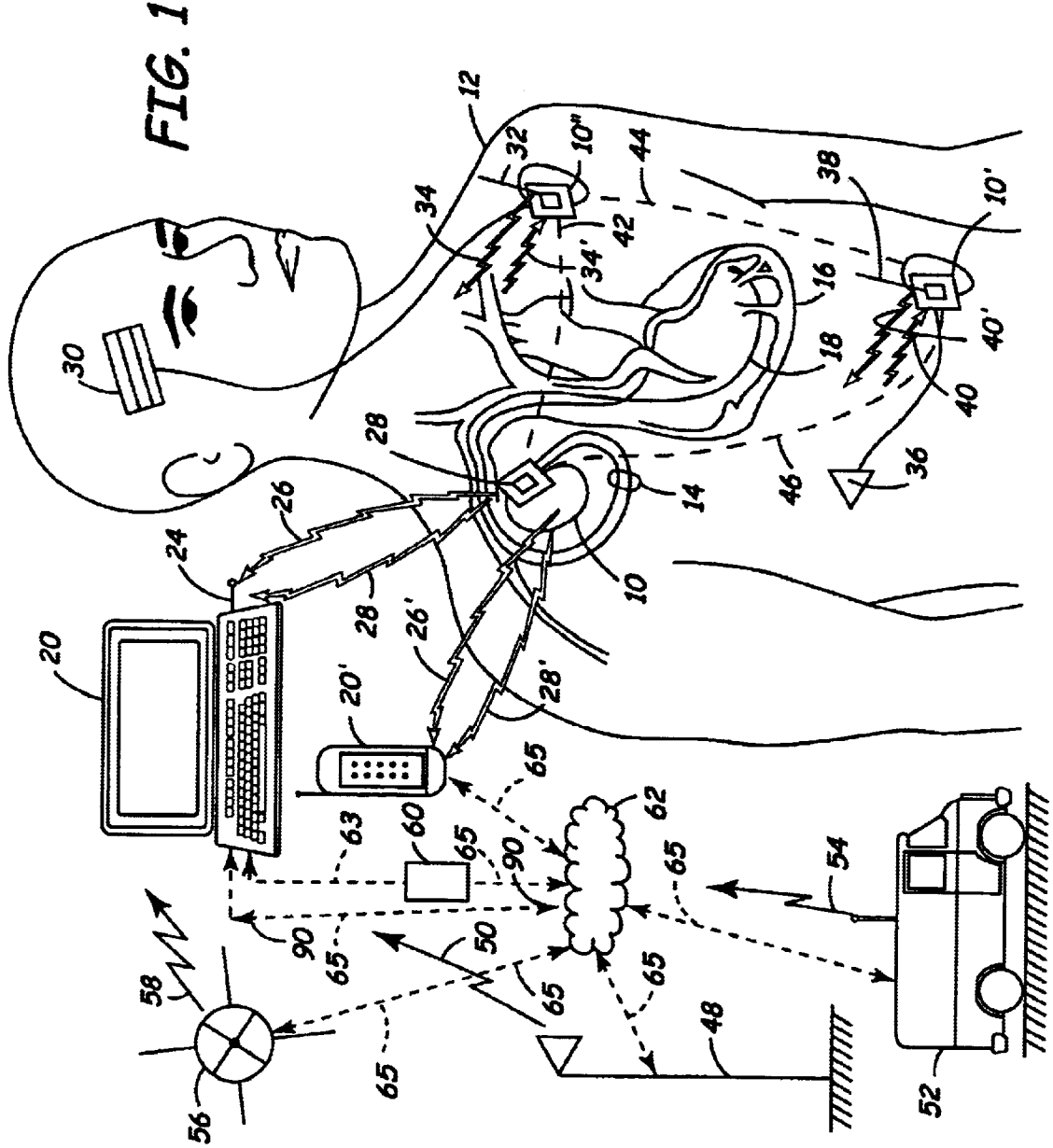
FIG. 1 is a simplified schematic diagram of major uplink and downlink telemetry communications providing IMD developed patient data from a plurality of IMDs through a programmer or webtop unit to a patient file at a centralized information database.
Figure 4:
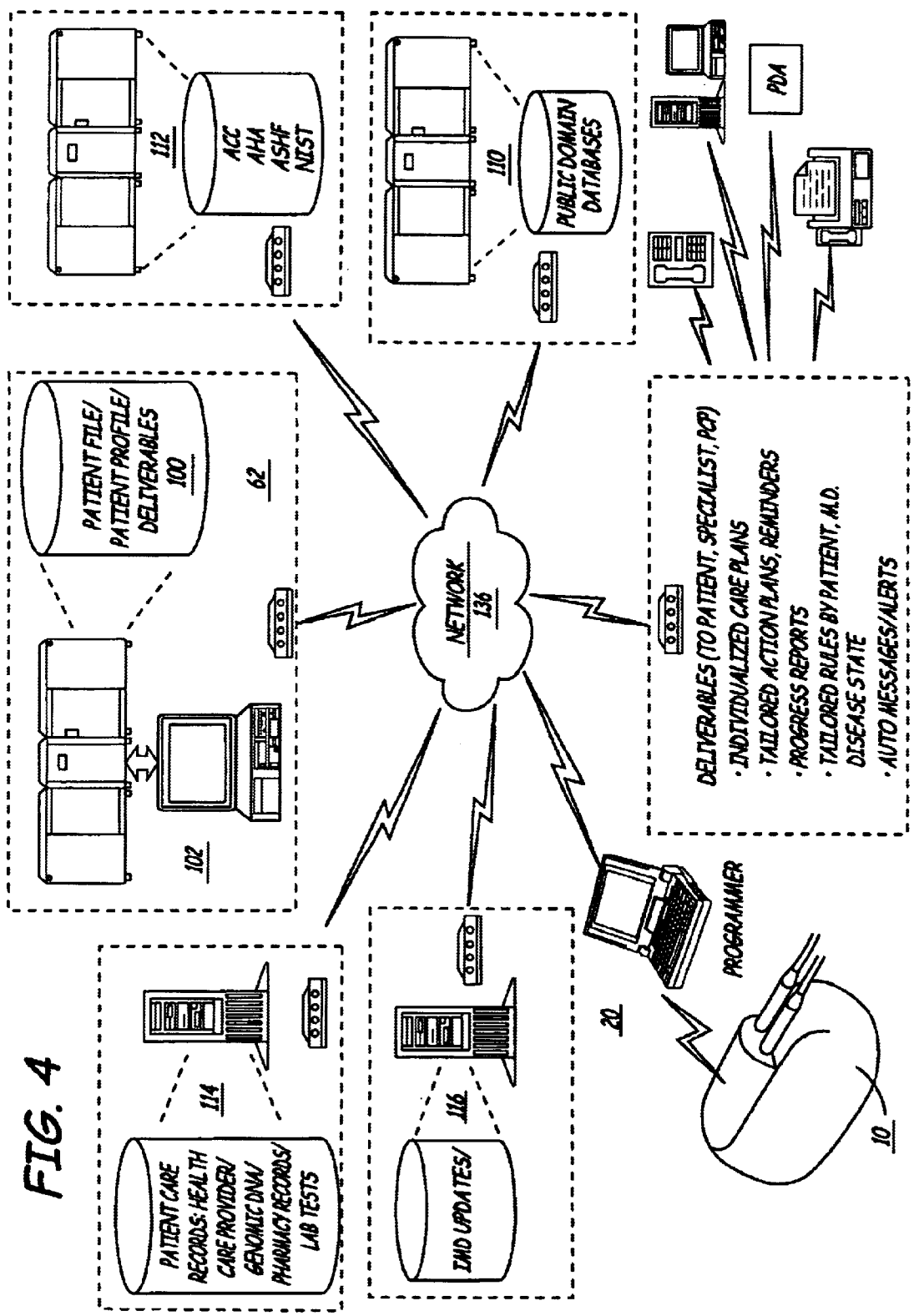
FIG. 4 is a representation of the major functional components of the expert data center of the present invention for managing the medical care of a patient, e.g., the patient of FIG. 1, having one or more IMD implanted in the patient's body to deliver a therapy and/or monitor a physiologic condition, and capable of developing and provides patient specific information or "deliverables" to the patient and/or health care provider for the patient.

FIG. 1 is a simplified schematic diagram of major uplink and downlink telemetry communications providing IMD developed patient data from a plurality of IMDs through a programmer or webtop unit to a patient file at a centralized information database in the system of FIG. 4. Specifically, a bi-directional wireless communications system between programmer 20, webtop unit 20', and a number of IMDs implanted in patient 12 beneath the skin or muscle and represented by IMD 10, IMD 10' and IMD 10" is shown. The IMDs are electrically coupled to electrodes 18, 30, and 36 respectively in a manner known in the art. IMD 10 contains a microprocessor for timing, sensing and pacing functions consistent with preset programmed functions. Similarly, IMDs 10' and 10" are microprocessor-based to provide timing and sensing functions to execute the clinical functions for which they are employed.

The IMDs contemplated by the present invention include a cardiac pacemaker, a defibrillator, a pacer-defibrillator, implantable monitor (Reveal and Chronicle), cardiac assist device, and similar implantable devices for cardiac rhythm and therapy. Further the IMD units contemplated by the present invention include electrical stimulators such as, but not limited to, a drug delivery system, a neural stimulator, a neural implant, a nerve or muscle stimulator or any other implant designed to provide physiologic assistance or clinical therapy. For example, IMD 10' could provide neural stimulation to the brain via electrode 30 and IMD 10" may function as a drug delivery system that is controlled by electrode 36.

The various functions of the IMDs are coordinated using wireless telemetry. Wireless links 42, 44 and 46 jointly and severally couple IMDs 10, 10' and 10" such that programmer 20 may transmit commands or data to any or all the of IMDs via one of telemetry antennas 28, 32 and 38. This structure provides a highly flexible and economical wireless communications system between the IMDS. Further, the structure provides a redundant communications system, which enables access to any one of a multiplicity of IMDs in the event of a malfunction of one or two of antennas 28, 32 and 38.

Programming commands or data are transmitted from programmer 20 to IMDs 10, 10', and 10" via external RF telemetry antenna 24. Telemetry antenna 24 may be an RF head or equivalent and may be located on programmer 20 externally on the case or housing. Telemetry antenna 24 may be generally telescoping and may be adjustable on the case of programmer 20. Both programmer 20 and webtop unit 20' may be placed a few feet away from patient 12 and would still be within range to wirelessly communicate with telemetry antennas 28, 32, and 38.

The centralized information database can comprise a remote, web-based, expert data center 62, hereinafter referred to as, interchangeably, "data center 62", "expert data center 62" or "web-based data center 62" without limitations. IMD developed patient data is first uplink telemetered to the programmer 20 or webtop unit 20' and then communicated to the expert data center 62 through programmer 20 or webtop unit 20'. Accordingly programmer 20 and webtop unit 20' function as an interface between IMDs 10, 10' and 10" and data center 62.

Various scalable, reliable and high-speed wireless communication systems can be employed to bi-directionally transmit high fidelity digital/analog data between programmer 20 or webtop unit 20' and data center 62. There are a variety of wireless mediums through which data communications could be established between programmer 20 or webtop unit 20' and data center 62. The communications link between programmer 20 or webtop unit 20' and data center 62 could be modem 60, which is connected to programmer 20 on one side at line 63 and data center 62 at line 64 on the other side. In this case, data is transferred from data center 62 to programmer 20 via modem 60. Alternate data transmission systems include, without limitations, stationary microwave and/or RF antennas 48 being wirelessly connected to programmer 20 via tunable frequency wave delineated by line 50. Antenna 48 is in communications with data center 62 via wireless link 65. Similarly, webtop unit 20', mobile vehicle 52 and satellite 56 are in communications with data center 62 via wireless link 65. Further, mobile system 52 and satellite 56 are in wireless communications with programmer 20 or webtop unit 20' via tunable frequency waves 54 and 58, respectively.

In the preferred embodiment a Telnet system is used to wirelessly access data center 62. Telnet emulates a client/server model and requires that the client run dedicated software to access data center 62. The Telnet scheme envisioned for use with the present invention includes various operating systems including UNIX, Macintosh, and all versions of Windows.

Functionally, an operator at programmer 20 or an operator at data center 62 would initiate remote contact with the programmer 20 or webtop unit 20'. Or the IMD 10 could initiate contact through the programmer 20 or webtop unit 20' with the data center 62 while the patient sleeps. Programmer 20 communicates with IMDs 10, 10' and 10" via link antennas 28, 32 and 38 to enable data reception and transmission. For example, an operator or a clinician at data center 62 may downlink to programmer 20 to perform a routine or a scheduled evaluation of programmer 20. In this case, the wireless communication is made via wireless link 65. If a downlink is required from programmer 20 to IMD 10 for example, the downlink is effected using telemetry antenna 22. In the alternate, if an uplink is initiated from patient 12 to programmer 20, the uplink is executed via wireless link 26. As discussed herein below, each antenna from the IMDs can be used to uplink all or one of the IMDs to programmer 20. For example, IMD 10" which relates to neural implant 30 can be implemented to up-link, via wireless antenna 34 or wireless antenna 34', any one, two or more IMDs to programmer 20. Preferably bluetooth chips or similar technology, adopted to function within the body to outside the body according to medical facility operating ranges, and also adopted to provide low current drain, are embedded in order to provide wireless and seamless connections 42, 44 and 46 between IMDs 10, 10' and 10". The communication scheme is designed to be broadband compatible and capable of simultaneously supporting multiple information sets and architecture, transmitting at relatively high speed, to provide data, sound and video services on demand.

FIG. 2 illustrates typical major operative structures common to all IMDs 10, 10' and 10" are represented in a generic format. In the interest of brevity, IMD 10 relative to FIG. 2 refers to all the other IMDs 10' and 10". Accordingly, IMD 10 is implanted in patient 12 beneath the patient's skin or muscle and is electrically coupled to heart 16 of patient 12 through pace/sense electrodes and lead conductor(s) of at least one cardiac pacing lead 18 in a manner known in the art. This is illustrated generally as therapy/monitory circuitry 70. IMD 10 contains timing control 72 including operating system that may employ microprocessor 74 or a digital state machine for timing, sensing and pacing functions in accordance with a programmed operating mode. IMD 10 also contains sense amplifiers for detecting cardiac signals, patient activity sensors or other physiologic sensors for sensing the need for cardiac output, and pulse generating output circuits for delivering pacing pulses to at least one heart chamber of heart 16 under control of the operating system in a manner well known in the prior art. The operating system includes memory registers or RAM/ROM 76 for storing a variety of programmed-in operating mode and parameter values that are used by the operating system. The memory registers or RAM/ROM 76 may also be used for storing data compiled from sensed cardiac activity and/or relating to device operating history or sensed physiologic parameters for telemetry out on receipt of a retrieval or interrogation instruction. All of these functions and operations are well known in the art, and many are generally employed to store operating commands and data for controlling device operation and for later retrieval to diagnose device function or patient condition.

Programming commands or data are transmitted between IMD 10 RF telemetry antenna 28, for example, and an external RF telemetry antenna 24 associated with programmer 20. In this case, it is not necessary that the external RF telemetry antenna 24 be contained in a programmer RF head so that it can be located close to the patient's skin overlying IMD 10. Instead, the external RF telemetry antenna 24 can be located on the case of programmer 20. It should be noted that programmer 20 can be located some distance away from patient 12 and still maintain a telemetry session communication link with IMDs 10, 10', and 10". For example, programmer 20 and external RF telemetry antenna 24 may be on a stand a few meters or so away from patient 12. Moreover, patient 12 may be active and could be exercising on a treadmill or the like during an uplink telemetry interrogation of real time ECG or other physiologic parameters. Programmer 20 may also be designed to universally program existing IMDs that employ RF telemetry antennas of the prior art and therefore also have a conventional programmer RF head and associated software for selective use therewith.

In an uplink telemetry session between IMD 10 and programmer 20, for example, telemetry transmission 22 is activated to operate as a transmitter and external RF telemetry antenna 24 operates as a telemetry receiver. In this manner, data and information may be transmitted from IMD 10 to programmer 20. In the alternate, IMD 10 RF telemetry antenna 26 operates as a telemetry receiver antenna to downlink data and information from programmer 20. Both RF telemetry antennas 22 and 26 are coupled to a transceiver comprising a transmitter and a receiver.

FIG. 3 is a simplified circuit block diagram of major functional components of programmer 20. The external RF telemetry antenna 24 on programmer 20 is coupled to a telemetry transceiver 86 and antenna driver circuit board including a telemetry transmitter and telemetry receiver. The telemetry transmitter and telemetry receiver are coupled to control circuitry and registers operated under the control of microcomputer 80. Similarly, within IMD 10, for example, the RF telemetry antenna 26 is coupled to a telemetry transceiver comprising a telemetry transmitter and telemetry receiver. The telemetry transmitter and telemetry receiver in IMD 10 are coupled to control circuitry and registers operated under the control of microcomputer 74.

Further referring to FIG. 3, programmer 20 is a personal computer type, microprocessor-based device incorporating a central processing unit, which may be, for example, an Intel Pentium microprocessor-based microcomputer 80 or the like. A system bus interconnects microcomputer 80 with a hard disk drive, storing operational programs and data, and with a graphics circuit and an interface controller module. A floppy disk drive or a CD ROM drive is also coupled to the bus and is accessible via a disk insertion slot within the housing of programmer 20. Programmer 20 further comprises an interface module, which includes a digital circuit, a non-isolated analog circuit, and an isolated analog circuit. The digital circuit enables the interface module to communicate with interface controller module. Programmer 20 is preferably of the type that is disclosed in U.S. Pat. No. 5,345,362.

In order for the physician or other caregiver or operator to communicate with the programmer 20, a keyboard or input 82 coupled to microcomputer 80 is optionally provided. However the primary communications mode may be through graphics display 84 of the well-known "touch sensitive" type controlled by a graphics circuit. A user of programmer 20 may interact therewith through the use of a stylus, also coupled to a graphics circuit, which is used to point to various locations on display 84 which display menu choices for selection by the user or an alphanumeric keyboard for entering text or numbers and other symbols. Various touch-screen assemblies are known and commercially available. Display 84 and or the keyboard comprise means for entering command signals from the operator to initiate transmissions of downlink or uplink telemetry and to initiate and control telemetry sessions once a telemetry link with data center 62 or an implanted device has been established. Display 84 is also used to display-patient related data and menu choices and data entry fields used in entering the data in accordance with the present invention as described below. Graphics display 84 also displays a variety of screens of uplink telemetered, stored or real-time generated, IMD developed patient data. Display 84 may also display uplink telemetered event signals as they are received and thereby serve as a means for enabling the operator to timely review link-history and status.

Programmer 20 is also provided with a strip chart printer or the like coupled to interface controller module so that a hard copy of a patient's ECG, EGM, marker channel, and other graphics displayed on the display screen can be generated. Various patient history data and IMD performance data may be printed out once a telemetry session is established between programmer 20 and any one of IMDs 10, 10' and 10".

The display and or the keyboard of programmer 20 preferably include means for entering command signals from the operator to initiate and control telemetry sessions once a telemetry link with one or more IMDs has been established. The graphics display 84 is also used to display patient-related data and menu choices and data entry fields used in entering the data. As will be appreciated by those of ordinary skill in the art, it is often desirable to provide a means for programmer 20 to adapt its mode of operation depending upon the type or generation of IMD to be programmed and to be compliant with the wireless communications system through which data and information is transmitted between programmer 20 and data center 62.

The present invention aids in solving the problem of bringing existing but widely scattered expert medical and biological knowledge and expertise into the routine (generally non-expert) treatment of chronic diseases through the combining of objective and subjective medical data into a database that allows sophisticated analysis and development of medical decision tools that allow the proliferation of "expert level" medical knowledge across the general medical community (for both clinical and research purposes). This technique alleviates the chronic problem that there are only a small number of "expert medical physicians" that deliver the optimal care to patients suffering from chronic diseases. General practitioners, family practice physicians, and internal medicine physicians, who don't possess the level of expertise necessary to provide the best care at reduced cost, care for an estimated 90% of chronic disease patients, even those who have received an IMD. The illustrated and described data management system provides a systematic and continuously updated approach to improving understanding and decision-making.

FIG. 4 is a representation of the major functional components of the expert data center 62 of the present invention for managing the medical care of a patient, e.g., the patient of FIG. 1, having one or more IMD 10, 10', 10" implanted in the patient's body to deliver a therapy and/or monitor a physiologic condition, and capable of developing and provides patient specific information or "deliverables" to the patient and/or health care provider for the patient.

Figure 5:
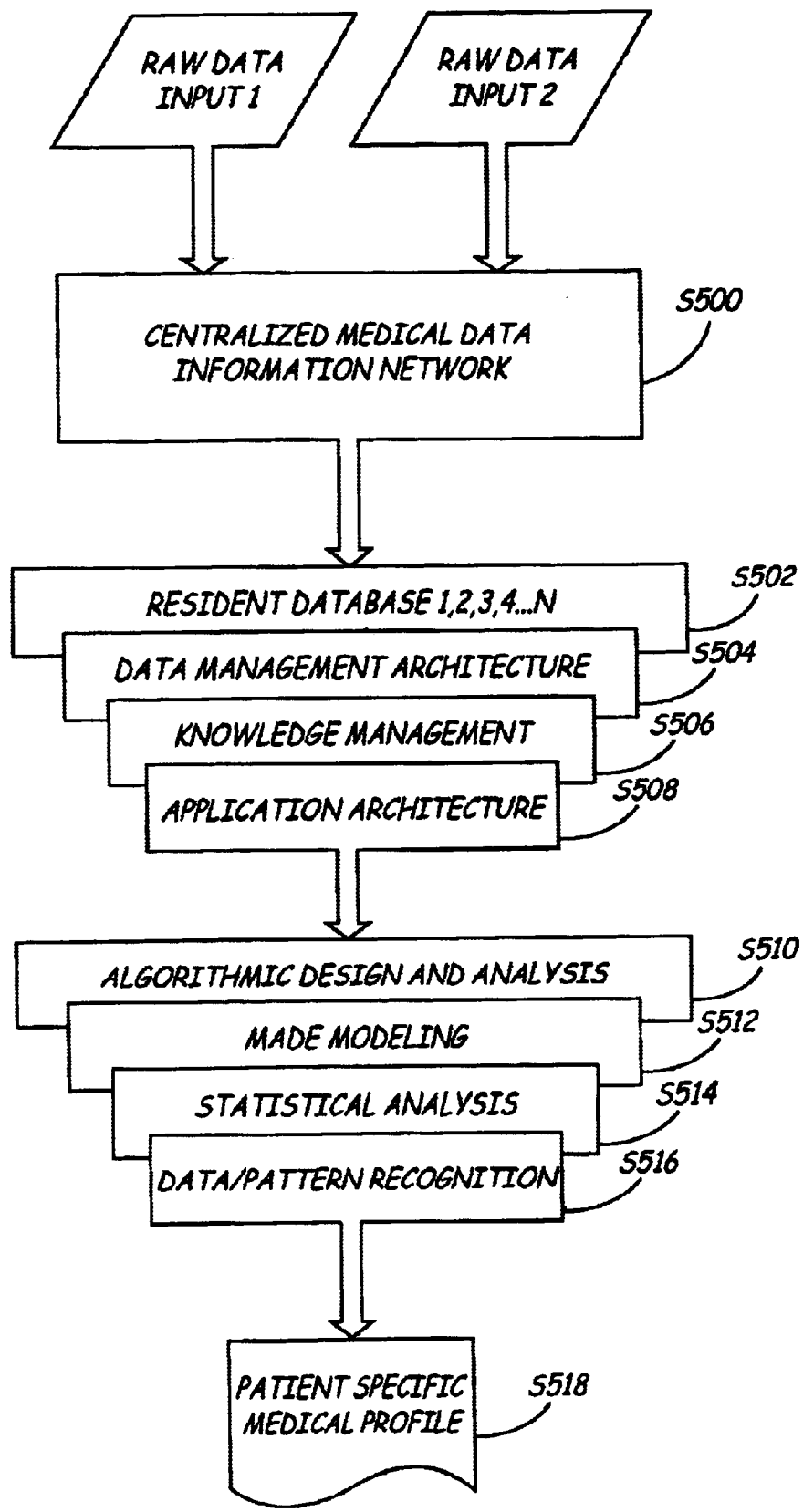
FIG. 5 is a chart illustrating the functions performed on data in the centralized medical data information network of FIG. 4.
Figure 6:
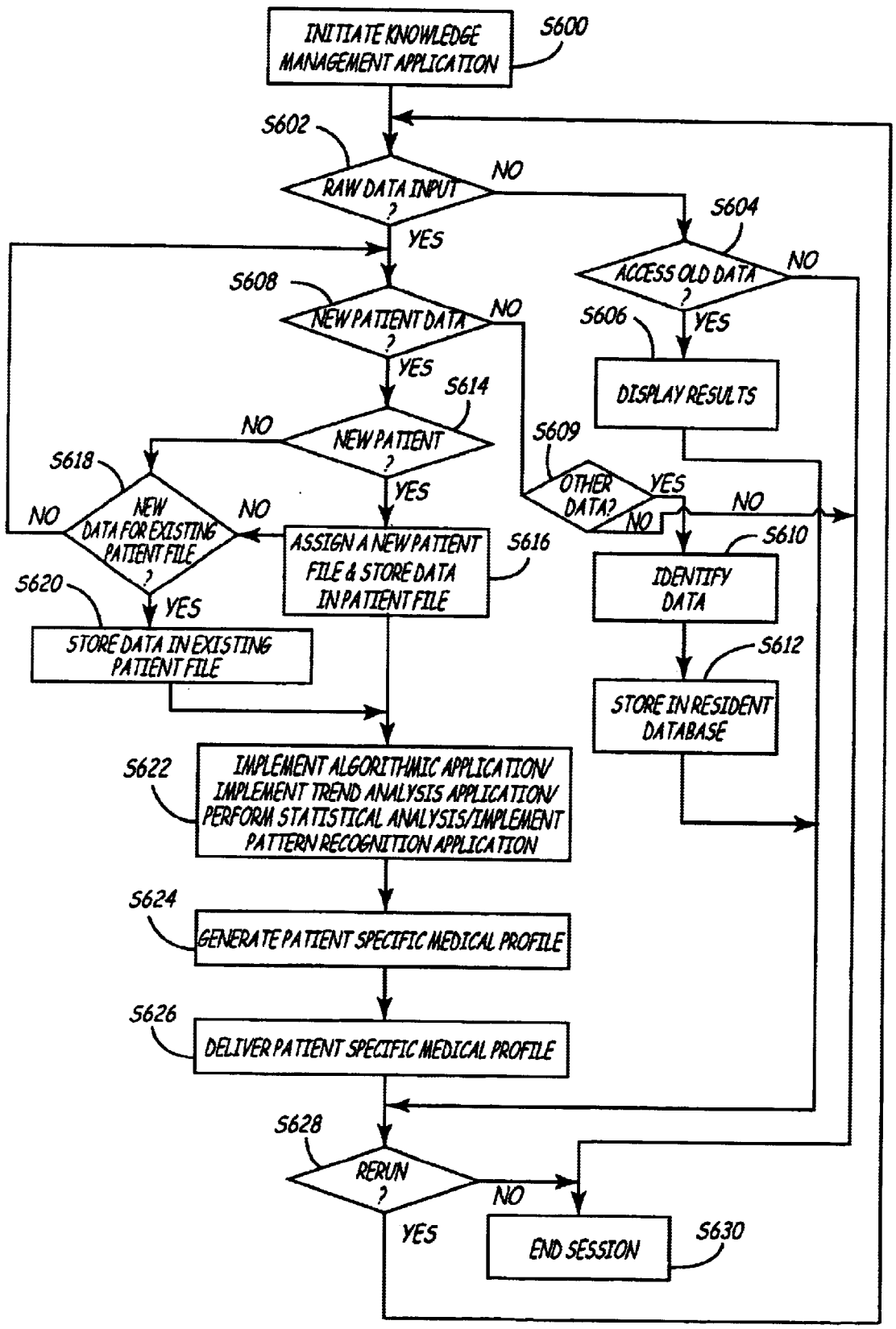
FIG. 6 is a flow chart illustrating the functions of processing patient data received in the centralized medical data information network of FIG. 4.
Figure 7:
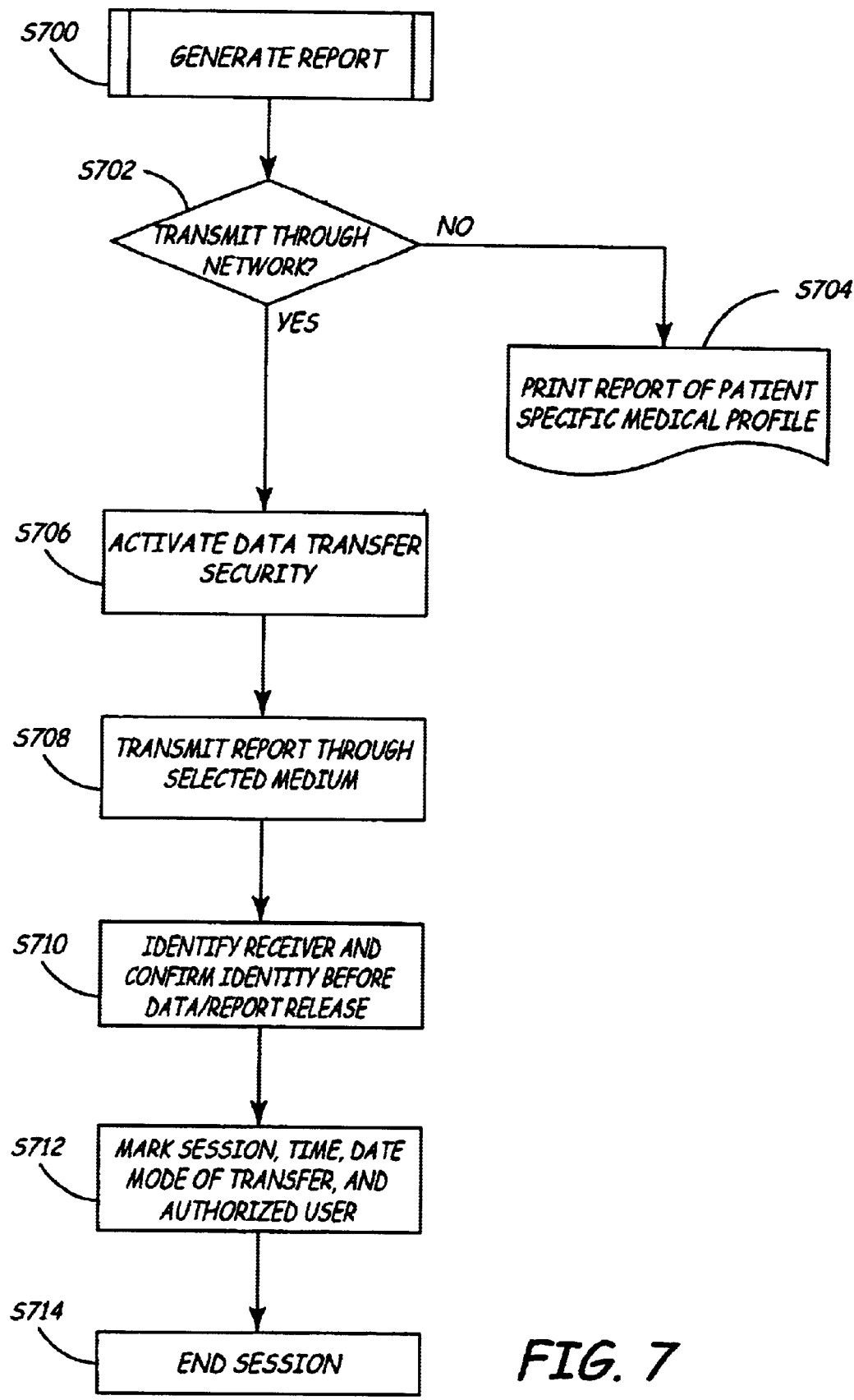
FIG. 7 is a flow chart illustrating the functions of delivering a patient specific medical profile through the medical data information network of FIG. 4.

FIG. 5 illustrates the tools brought to bear in the system 62 as further described below. These tools develop and update a patient-specific medical profile as also shown in the steps of FIG. 6, and further deliver the patient-specific medical profile as shown in the steps of FIG. 7.

The centralized medical information network or data center 62 has data resources 102 maintaining centralized database 100. This network applies deep computing technologies to the assembled body of data in database 100 and provides the deliverables to the patient and/or the health care provider for the patient. The data resources 102 receive the IMD-developed patient data and also receive, or have access to, other patient data derived from other sources via the network 136. Data may be received from sources such as manufacturer's and government repositories, and the large body of general healthcare information residing within established public domain databases and governmental and international health agency databases.

Data resources 102 represent a high-speed computer network system which is located in remote expert data center 62 having wireless bi-directional data, voice and video communications with programmer 20 via the network and wireless communications links. Generally data resources 102 are preferably located in a central location and are equipped with high-speed web-based computer networks. Preferably, the data resource center is manned 24-hours by operators and clinical personnel who are trained to provide a web-based remote service to programmer 20. The location of remote data center 62 and, consequently, the location of data resources 102 are dependent upon the sphere of service. In accordance with the present invention, data resources 102 may be located in a facility of the company that manufactures programmer 20 and the IMDs 10, 10', 10" or in a health care delivery management facility. The wireless data communications network 136 can constitute a plurality of links or interfaces, such as a local area network (LAN), an Internet connection, a telephone line connection, a satellite connection, a global positioning system (GPS) connection, a cellular connection, a laser wave generator system, any combination thereof, or equivalent data communications links.

Data resources 102 and database 100 of data center 62 are coupled through the network 136 to receive or retrieve information and data from public domain databases 110 and specific national and international health organizations and government and educational agencies 112, the patient-specific data accumulated by health care providers in one or more patient health care database 114, IMD data relating to the specific IMD, which is typically provided by the manufacturer's device database 116, and IMD-developed data from the IMD 10 itself, in this case transmitted by programmer 20. The present invention advantageously provides patient-specific, individualized, information for IMD-bearing patients that draws upon worldwide expertise and knowledge of IMDs of the type implanted, the patient's disease etiology, the drugs prescribed to the patient, the knowledge of experts in the field, and the optimal modes of operating the IMD to monitor physiologic conditions or apply therapies as reported by experts and medical device manufacturers.

The overall concept embodied in the system of FIG. 4 operate in accordance with the processes illustrated in FIGS. 5–7 to integrate, structure, analytically process, and apply deep computing techniques to the data derived by IMD 10 (and any other IMDs implanted in the patient). Other patient data developed by the health care providers from disparate data bases, and general healthcare information is analyzed in a similar manner to develop new and unique clinical tools to help physicians better manage chronically ill patients (i.e. improve diagnosis, monitoring, and therapy effectiveness/optimization).

As a first step, it is understood that individual patient data often resides in independent and unrelated databases 114 or record keeping systems. These databases or record keeping systems include those that reside with the physician or healthcare provider of the patient, implanted medical devices (in the case of an implanted medical device patient), and other databases oftentimes associated with the treatment and diagnosis of patients.

The patient data from database 114 provided to the patient file in database 100 can include all available patient records, patient laboratory test data of laboratory tests of the patient, clinical test data of clinical tests of the patient, pharmaceutical prescription data of drugs prescribed for the patient, other data accumulated by those providing medical care to the patient, including physical examination records, reports of results of echocardiography and radiographic imaging, patient and family member reported symptoms, signs and symptoms data reported by the patient. Patient data can also be collected through an interactive voice telephony system via telephone data entry.

The patient data in databases 114 derived from other sources than the IMD developed patient data and provided to the patient file in database 100 can also include the patient's genomic data (DNA). In the cardiac monitoring context, significant information about drug interaction and heart irregularities could be correlated with specific DNA signatures. Gene expression tools used to study drug-disease interactions can be extended to develop diagnostic algorithms, monitoring indicators and individual therapies based on deeper knowledge resulting from integrating and analyzing gene expression profiles with IMD developed patient data, drug regimens, and other relevant clinical/patient information. Moreover, databases 114 maintained by private insurance companies and public government sponsored health care payment agencies could be accessed to provide medical claims data relating to the individual patient.

Other independent databases 112 are also available. For example, databases maintained by medical societies and research institutions possess or manage large amounts of data that is accumulated and processed in the course of conducting research on disease etiology, disease prevalence, diagnostic algorithms, care guidelines, etc. For example, the American College of Cardiology, the American Heart Association, the Framingham study database, and the European Society of Cardiology all have databases of such data and care guideline standards that are used in the course of treating patients worldwide. The above-referenced '542 patent describes a National Institute of Standards and Technology medical knowledge bank, specifically a multi-media object relational database system (MORDBS) which, if implemented could be drawn upon as one of the independent databases 112. The independent databases can also include those providing clinical assessment tools, e.g., the "Living with Heart Failure Quality of Life Assessment" tool developed by the University of Minnesota.

There are also public domain databases 110, often supported by non-profit research organizations which contain databases regarding diseases, disease treatment, and healthcare research statistics that are openly available to both the public and research communities as an aid to further and support ongoing medical research. Examples of these databases include the National Heart Lung and Blood Institute, National Institute of Health, Center for Disease Control, and others that reside in medical research organizations or universities. The data center 62 or the present invention draws together these disparate sources of data together with the IMD developed data into a medical database infrastructure capable of organizing and warehousing this data in a manner that allows for high performance computing power to apply systematic and highly sophisticated analytical techniques in order to develop unique and new understanding regarding disease in general as well as the individual status of patients undergoing diagnosis and treatment over the course of managing their disease.

Both research and clinical applications are drawn together that can result in improved diagnosis, therapy, monitoring, and patient outcomes to help physicians better identify and manage chronically ill patients having IMDs. The long-term vision of the system of the present invention also involves integrating individual genomic data with the aforementioned patient clinical information and general healthcare statistics and IMD data from database 116 and IMD developed patient data from programmer 20 to enable the application of personalized medicine to the patient having the IMD. The IMD developed patient data collected by the IMD (or IMDs) is integrated with other individual patient data (clinical data, family history, DNA, etc., from patient database 114) and analyzed with respect to relevant clinical information about the patient. Significant information about drug effectiveness, drug interactions, physiologic heart regularities and other patient status conditions could be correlated with specific DNA signatures.

The present invention in a preferred embodiment as illustrated in FIGS. 4 and 5 operates by providing patient data from databases 114 and IMD developed patient data to a patient file maintained at the centralized information database as shown in steps S600–S620 of FIG. 6. In step S602, raw patient data is added to the patient file. If the data is new patient data, and if the patient is a new patient, a new file is opened, as shown in steps S614 and S616. Otherwise, the new patient data is added to an existing file in step S620.

After the new patient data is stored in the correct file, the patient data may be processed, as shown in step S622. This may include invoking a trend analysis, statistical analysis, or pattern recognition application. Statistical data from public domain databases 110 and governmental and international health agency databases 112 is accessed, and deep computing techniques are applied to mine the accessed statistical data, and to associate pertinent statistical data with the patient data in the patient file to form a patient specific medical profile.

Deep computing technologies implemented in step S622 may further include applying one or more of algorithmic design and analysis, mathematical modeling and trend analysis, statistical estimation, and data/pattern recognition to the statistical data. In this manner, relevant statistical data may be associated with the patient data to form the patient-specific medical profile. These technologies may also incorporate data mining techniques to derive useful information from very large sets of data. Interpolation and approximation methods may be applied to the data to estimate trends associated with dynamic variables such as patient status. Pattern discovery algorithms may be utilized to locate recurring events in large, continuous streams of information. Such patterns are inherent in EKG's, cardiac pressure waveforms, and other physiologic data. Pattern recognition techniques are particularly useful when patient data is received over a long-term period from the IMD. Cluster analysis mechanisms may then be applied to determine the meaning of low frequency events or patterns that possess similarities. Other statistical methods and predictive algorithms may be utilized to determine the relevance of both low and high-frequency data events. Another useful technique involves text mining, wherein textual information is read via an automated process, then analyzed to discover insights related to a patient health condition.

Neural networks and fuzzy logic may be applied to process the patient data. This involves utilizing expert systems and relational databases based on predictive algorithms establish health trends, and develop and patient-specific therapy regimen. This is described in more detail in FIG. 5 to be discussed further below.

After the data is processed, the patient-specified medical profile is generated, in step S624. The formulating step S624 comprises formulating one or more of an individualized care plan, tailored action plans and reminders, progress reports, tailored rules by patients, physician and disease state, and automatically generated messages and alerts. In addition to clinical patient management tools including individualized care plans, therapy optimization guidelines and rules, tailored care action plans, and reminders, the system provides personalized teaching and educational messages for the patient based on their disease state and individualized care plans and health progress reports. All of these capabilities optimize medical management to the individual level compared to today's medical practice where individuals are treated under the auspices of group or total population care guidelines and generic care plans and therapies.

More refined decision support tools based on this new understanding will evolve over time. All of this newly discovered and created insight and understanding allows development and results in the deliverables listed in the illustration of FIG. 4. These deliverables, along with associated teaching and educational tools and messages will be accessed and used by physicians, nurses, healthcare researchers, patients, and family members in a variety of manual and electronic means including paper, telephone (interactive voice telephony), cell phones, personal digital assistants, and other data access devices as they become available. This is an important point in the aforementioned need to solve the problem of proliferating expert medical care, practices, information, and education across the general medical communities and public community at large.

After the profile is generated, it may be delivered to the patient-specific medical profile, as shown in step S626. The delivered profile contains formulated patient specific information that is delivered as a "deliverable" of FIG. 4 to the patient and/or one or more health care provider. Step 626 is described in more detail in FIG. 7.

The patient specific medical profile is updated continually as additional or new patient data is entered in over the course of the patient's life/treatment regimen by repeating steps S600–S626, as indicated by step 628.

Returning to Step S602, if new raw data is not available, old data may be accessed from the patient profile, and data and/or trends and analysis results may be displayed, as shown in steps S604 and S606.

Finally, in Step S608 other data may be received in the system that is not necessarily patient-specific data. For example, health care data related to trends and statistics regarding the general population may be received from an external source such a public domain database or governmental database, as discussed above. If such data is provided, it may be identified and stored in the resident database, as shown in steps S609, S610 and S612. This data may then be used to perform the processing steps illustrated generally as step S622. If data that is not of interest is received in step S609, the session may be ended, as indicated by step S630.

The time element associated with this database and analytical learning process cannot be overestimated. As the database itself becomes more rich, more populated in terms of absolute data points, and the variety of data points, coupled with the ongoing advances in high performance computing and analytical techniques, over time the database will become smarter and smarter resulting in more effective health management tools and understanding. In this regard, patient specific data alone is not enough. The patient data must be combined systematically with both analytical techniques, data organization/infrastructure methodologies, and most importantly current and generally accepted and advancing medical knowledge and care guidelines associated with specific diseases. All of these combined are necessary for this system to solve the problem it is seeking to solve and provide the benefits hypothesized in the form of improved care at reduced cost.

There are several short-term and long-term opportunities to apply deep computing and knowledge management technologies to the IMD developed patient data and other patient data together with data from the other databases 110, 112 and 116 to analyze very large data sets and find relationships, patterns and trends that were previously unknown or unseen. One area of application would be in analyzing the large amount of parametric data from implanted monitors, such as the above-referenced Chronicle IMD. Data can be uploaded for data analysis and pattern discovery to find relationships difficult in subjective interpretation and existing tools. Pattern matching technology can then be applied to compare unusual patterns to known or understood patterns. Such analysis could accelerate understanding of the IMD developed patient data and the possibility of individualized, real-time event prediction, prevention and care guidelines. Another near-term possibility is to combine deep computing technologies that work on mining and manipulating very large data sets (which have been applied in the life sciences) with knowledge sharing technologies that could make the "digested" data available to physicians, practitioners, and researchers.

Based on this understanding, "On-line Algorithms" could be developed as a clinical decision making tool that highlights significant variations from the norm, or predict future clinical trends based on continuously acquired and analyzed data. These applications should speed and deepen our understanding of the etiology, progression and treatment of heart failure and other related cardiovascular co-morbidities (such as VT/VF, neurology, diabetes, etc.).

Returning to FIG. 5, this flowchart describes steps S622 and S624 in more detail. Centralized medical data from the data information network is derived from raw patient data in Step S500. This is processed using a data processing system that may include, or have access to, one or more resident database, a data management architecture, knowledge management capabilities, and applications programs such as those described above. This is shown in Steps S502–S508, respectively. Various techniques may be applied to the data, including design and analysis algorithms, math modeling, statistical analysis, and data pattern recognition, as indicated by steps S510–S516. The results are then assembled into a patient-specific medical profile, as indicated by steps S518.

Turning now to FIG. 7, this flowchart shows in steps S700–S714 the functions of delivering a patient-specific medical profile through the medical data information network of FIG. 4 to a patient or medical care provider authorized to receive it. Step S700 comprises step S624 of FIGS. 5 and 6. Security steps S706–S712 are invoked and practiced to ensure that a patient specific medical profile is transferred securely through the network in step S702 to an authorized receiver. A hardcopy of the patient specific medical profile may be available in step S704 if data transmission is not desired.

It will be understood that certain of the above-described structures, functions and operations of the pacing systems of the preferred embodiments are not necessary to practice the present invention and are included in the description simply for completeness of an exemplary embodiment or embodiments. In addition, it will be understood that specifically described structures, functions and operations set forth in the above-referenced patents can be practiced in conjunction with the present invention, but they are not essential to its practice. All such listed patents and publications are incorporated herein by reference in their entireties. It is therefore to be understood, that within the scope of the appended claims, the invention may be practiced otherwise than as specifically described without actually departing from the spirit and scope of the present invention.

What is claimed is:

1. A method of managing the medical care of a patient having one or more implantable medical device implanted in the patient's body to deliver a therapy and/or monitor a physiologic condition of the patient and capable of communicating patient data externally to a remote receiver comprising the steps of:

provessing patient data to a patient file at a centralized information database, the patient data including implantable medical device developed patient data;

accessing statistical data from public domain databases and governmental and international health agency databases;

applying deep computing techniques to mine the accessed statistical data to associate pertinent statistical data with the patient data in the patient file to form a patient specific medical profile;

based upon the patient specific medical profile, formulating patient specific information; and delivering the formulated patient specific information to one or more of the patient and the health care provider providing care to the patient.

2. The method of claim 1, wherein the providing step further comprises providing device-related data of the implantable medical device implanted in the patient to the patient file.

3. The method of claim 1, wherein the providing step further comprises providing patient laboratory test data of laboratory tests of the patient to the patient file.

4. The method of claim 1, wherein the providing step further comprises providing clinical test data of clinical tests of the patient to the patient file.

5. The method of claim 1, wherein the providing step further comprises providing pharmaceutical prescription data of drugs prescribed for the patient to the patient file.

6. The method of claim 1, wherein the providing step further comprises providing patient related care provider data accumulated by the care providers providing medical care to the patient to the patient file.

7. The method of claim 6, wherein the patient related care provider data includes physical examination records and patient reported symptoms.

8. The method of claim 1, wherein the step of providing statistical data to the centralized information database is effected over a network.

9. The method of claim 1, wherein the step of providing patient data to the centralized information database is effected over a network.

10. The method of claim 1, wherein the step of delivering the formulated patient specific information is effected over a network.

11. The method of claim 1, wherein the formulating step further comprises formulating one or more of an individualized care plan, tailored action plans and reminders, progress reports, tailored rules by patients, physician and disease state, and automatically generated messages and alerts.

12. The method of claim 1, wherein the applying step further comprises applying one or more of algorithmic design and analysis, mathematical modeling and trend analysis, statistical estimation, and data/pattern recognition to the statistical data based upon the patient data to effect the association of relevant statistical data with the patient data to form the patient specific medical profile.

13. A computer-implemented software system of a centralized medical data information network for processing or deriving a patient specific medical profile to facilitate provision of medical care by medical care providers involving prescribing therapies delivered to the patient through operation of an implantable medical device implanted in the patient, the software system comprising:

inputting means for inputting data from various sources including implantable medical device developed patient data;

compiling means for compiling said inputted data from various sources into compiled data;

integrating means for integrating said compiled data with resident data in a centralized medical data information network into a patient file; and analysis performing means for performing analysis of the patient file to generate the patient specific medical profile;

wherein said inputting means, said compiling means, said integrating means and said analysis performing means are functional structures of said centralized medical data information network.

14. The software system of claim 13, wherein the patient specific medical profile enables medical caregivers to dispense, adjust, modify and/or anticipate therapy regimens, including therapy regimens delivered by said implantable medical device.

15. The software system of claim 13, wherein the inputting means further comprises means for allowing device-related data of the implantable medical device implanted in the patient to be compiled and integrated into the patient file.

16. The software system of claim 13, wherein the inputting means further comprises means for providing patient laboratory test data indicating patient laboratory tests to be compiled and integrated into the patient file.

17. The software system of claim 13, wherein the inputting means further comprises means for providing clinical test data of patient clinical tests to be compiled and integrated into the patient file.

18. The software system of claim 13, wherein the inputting means further comprises means for providing pharmaceutical prescription data of drugs prescribed for the patient to be compiled and integrated into the patient file.

19. The software system of claim 13, wherein the inputting means further comprises means for providing patient-related care provider data accumulated by the care providers providing medical care to the patient to be compiled and integrated into the patient file.

20. The software system of claim 19, wherein the patient-related care provider data includes physical examination records and patient reported symptoms.

21. The software system of claim 13, wherein the inputting means further comprises means for providing statistical data to the centralized information database over a network.

22. The software system of claim 13, wherein the inputting means further comprises means for providing patient data to the centralized information database over a network.

23. The software system of claim 13, further comprising means for delivering the patient-specific medical profile over a network to one or more of the medical care provider and the patient.

24. The software system of claim 13, wherein the analysis performing means further comprises means for formulating one or more of an individualized care plan, tailored action plans and reminders, progress reports, tailored rules by patients, physician and disease state, and automatically generated messages and alerts.

25. The software system of claim 13, wherein the integrating means applies deep computing techniques involving one or more of algorithmic design and analysis, mathematical modeling and trend analysis, statistical estimation, and data/pattern recognition to the statistical data based upon the patient data to effect the association of relevant statistical data with the patient data to form the patient specific medical profile.

26. A computer-implemented dynamic data and knowledge management software system of a centralized medical data information network implemented for chronic patient management to support diagnostic and therapy related medical decisions on an on-going basis in the form of a patient specific medical profile for a patient having one or more implantable medical device implanted in the patient, the software system comprising:

inputting means for inputting data from various sources and including implantable medical device-developed patient data;

compiling means for compiling said inputted data from various sources into compiled data;

integrating means for integrating said compiled data with resident data in a centralized medical data information network into a patient file; and analysis performing means for performing deep computing techniques upon the patient file to generate the patient specific medical profile.

27. The software system of claim 26, wherein the patient-specific medical profile enables medical caregivers to dispense, adjust, modify and/or anticipate therapy regimens, including therapy regimens delivered by said implantable medical device.

28. The software system of claim 26, wherein the inputting means further comprises providing device related data of the implantable medical device implanted in the patient to be compiled and integrated into the patient file.

29. The software system of claim 26, wherein the inputting means further comprises means for providing patient laboratory test data of laboratory tests of the patient to be compiled and integrated into the patient file.

30. The software system of claim 26, wherein the inputting means further comprises means for providing clinical test data of clinical tests of the patient to be compiled and integrated into the patient file.

31. The software system of claim 26, wherein the inputting means further comprises means for providing pharmaceutical prescription data of drugs prescribed for the patient to be compiled and integrated into the patient file.

32. The software system of claim 26, wherein the inputting means further comprises means for providing patient related care provider data accumulated by the care providers providing medical care to the patient to be compiled and integrated into the patient file.

33. The software system of claim 32, wherein the patient-related care provider data includes physical examination records and patient reported symptoms.

34. The software system of claim 26, wherein the inputting means further comprises means for providing statistical data to the centralized information database over a network.

35. The software system of claim 26, wherein the inputting means further comprises means for providing patient data to the centralized information database over a network.

36. The software system of claim 26, further comprising means for delivering the patient specific medical profile over a network to one or more of the medical care provider and the patient.

37. The software system of claim 26, wherein the analysis performing means further comprises means for formulating one or more of an individualized care plan, tailored action plans and reminders, progress reports, tailored rules by patients, physician and disease state, and automatically generated messages and alerts.

38. The software system of claim 26, wherein the deep computing techniques involving one or more of algorithmic design and analysis, mathematical modeling and trend analysis, statistical estimation, and data/pattern recognition to the statistical data based upon the patient data to effect the association of relevant statistical data with the patient data to form the patient specific medical profile.

* * * * *